US009040754B2

(12) United States Patent
Osborne et al.

(10) Patent No.: US 9,040,754 B2
(45) Date of Patent: May 26, 2015

(54) PRODUCT RECOVERY PROCESS IN THE FILTRATION OF POLYETHER POLYOLS

(75) Inventors: Robert B. Osborne, Wilmington, DE (US); Willard L. Quon, Houston, TX (US)

(73) Assignee: INVISTA North America S.a r.l., Wilmington, DE (US)

( * ) Notice: Subject to any disclaimer, the term of this patent is extended or adjusted under 35 U.S.C. 154(b) by 0 days.

(21) Appl. No.: 14/233,018

(22) PCT Filed: Jul. 17, 2012

(86) PCT No.: PCT/US2012/046998
§ 371 (c)(1),
(2), (4) Date: Apr. 3, 2014

(87) PCT Pub. No.: WO2013/012833
PCT Pub. Date: Jan. 24, 2013

(65) Prior Publication Data
US 2014/0303405 A1  Oct. 9, 2014

Related U.S. Application Data

(60) Provisional application No. 61/509,499, filed on Jul. 19, 2011.

(30) Foreign Application Priority Data

Oct. 28, 2011 (CN) .......................... 2011 1 0333661

(51) Int. Cl.
C07C 41/34 (2006.01)
C07C 41/46 (2006.01)
C08G 65/20 (2006.01)
C08G 65/30 (2006.01)

(52) U.S. Cl.
CPC ................. *C07C 41/34* (2013.01); *C07C 41/46* (2013.01); *C08G 65/20* (2013.01); *C08G 65/30* (2013.01)

(58) Field of Classification Search
None
See application file for complete search history.

(56) References Cited

U.S. PATENT DOCUMENTS

| 4,120,903 A | 10/1978 | Pruckmayr et al. |
| 4,137,396 A | 1/1979 | Louvar et al. |
| 4,306,943 A | 12/1981 | Mori et al. |
| 4,460,796 A | 7/1984 | Mueller |
| 4,985,551 A | 1/1991 | Perry et al. |
| 5,284,980 A | 2/1994 | Pruckmayr et al. |
| 5,410,093 A | 4/1995 | Dorai |
| 6,037,381 A | 3/2000 | Beer et al. |

FOREIGN PATENT DOCUMENTS

| WO | 9623019 A1 | 8/1996 |
| WO | 2010120289 A1 | 10/2010 |
| WO | 2011075177 A1 | 6/2011 |

OTHER PUBLICATIONS

Moon, Kihwan, International Preliminary Report on Patentability dated Jan. 21, 2014, for International Application No. PCT/US2012/046998, 6 pages.
O'Sullivan, Timothy, International Search Report dated Jul. 16, 2013, for International Application No. PCT/US2012/046998, 4 pages.

*Primary Examiner* — Brian J Davis
(74) *Attorney, Agent, or Firm* — Ni Yan

(57) ABSTRACT

An improved method for recovering a purified polyether polyol comprising the steps of providing an aqueous solution of a polyether polyol containing an alkali metal catalyst residual formed from a transesterification process, contacting the aqueous solution with a stoichiometric excess of magnesium sulfate to form a second aqueous solution, removing water from said second aqueous solution at a temperature above the melt temperature of said polyether polyol to produce a dehydrated slurry containing a molten polyether polyol phase essentially free of residual alkali metal and a precipitated solid phase comprising sulfate and/or sulfite salts of the alkali metal catalyst, magnesium hydroxide, and excess magnesium sulfate and/or sulfide, passing the dehydrated slurry of through a filtration system comprising a filtration press to separate the molten polyether polyol phase from the precipitated solid phase, wherein the filtration press is treated with a filter aid that is essentially free of transition metal oxide content, separating the molten polyether polyol phase substantially free of water, residual alkali metal catalyst and transition metal contaminants from the precipitated solid phase and recovering polyether polyol from the separated polyether polyol phase.

7 Claims, 1 Drawing Sheet

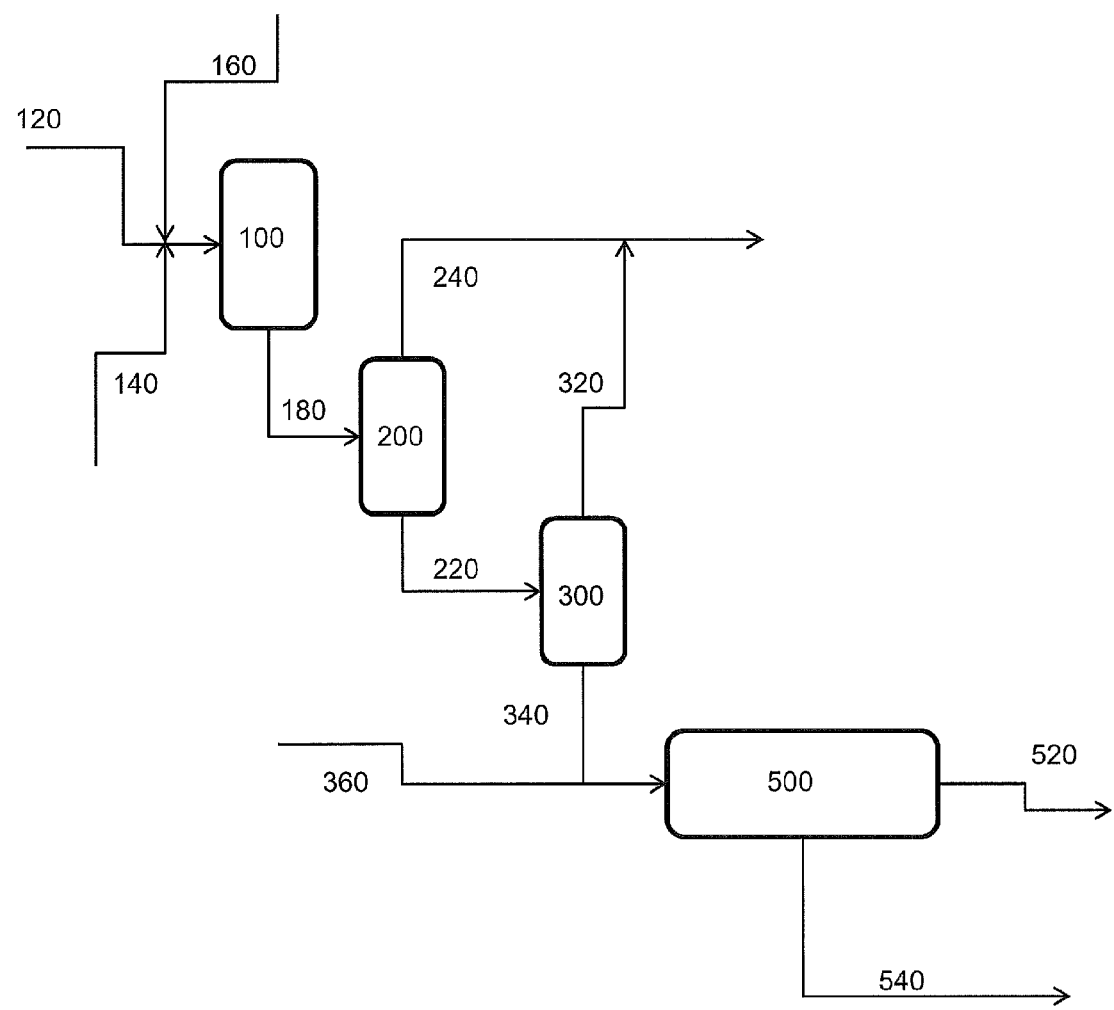

PRODUCT RECOVERY PROCESS IN THE FILTRATION OF POLYETHER POLYOLS

CROSS-REFERENCE TO RELATED APPLICATION

This application claims benefit of priority from U.S. Provisional Application No. 61/509,499, filed 19 Jul. 2011 and Chinese Patent Application No. 201110333661.2, filed 28 Oct. 2011. This application hereby incorporates both applications in their entirety.

FIELD OF THE INVENTION

This disclosure relates to a process for producing polyether polyols. More specifically, it relates to a process for removing a metal catalyst remaining from a transesterification step to recover a purified polyether polyol product.

BACKGROUND OF THE INVENTION

Homopolymers of THF, also known as polytetramethylene ether glycols (PTMEG), are well known for use in spandex, polyurethanes and other elastomers. These homopolymers impart superior mechanical and dynamic properties to polyurethane elastomers, fibers and other forms of final products. As discussed in U.S. Pat. No. 4,120,903, the polymerization process of utilizing tetrahydrofuran (THF) to manufacture polytetramethylene etherglycol (PTMEG) by passing through the intermediate PTMEA (i.e., PTMEG diacetate) has been commercially practiced since about 1997. The process involves a ring-opening of THF using perfluorosulfonic acid ionomer resin as the first step in the production of the PTMEA. The most commonly known process to convert PTMEA to PTMEG is by a conventional transesterification using an alkali metal catalyst, such as sodium methylate. This method results in a residual catalyst which needs to be removed from the PTMEG product.

There are many known processes for removing the remaining alkali metal catalyst from the PTMEG product after the transesterification step. Some of these known processes are disclosed in U.S. Pat. Nos. 4,137,396, 4,985,551, 4,460,796, 4,306,943 and 6,037,381. U.S. Pat. No. 5,410,093, herein incorporated in its entirety by reference, relates to a method wherein the alkali metal catalyst is neutralized in an aqueous media in the presence of an excess of magnesium sulfate. The inorganic co-products of this neutralization can include sodium sulfate and magnesium hydroxide. The various inorganic solids present in PTMEG are then separated in a chamber plate filter press operation. The filter press utilizes a filter cloth to aid in the removal of solids from the filtrate.

Filtration of solutions containing gelatinous solids is extremely difficult and slow through normal filter cloths and generally blinding of the cloth occurs with consequent cessation of flow through the filter. Normal procedure for the improvement in filtration rate involves the use of a filter aid which protects the filter cloth and retains an open structure allowing sufficient flow of filtrate and also clarification of the suspended solids by entrapment in the porous cake. Therefore, it was observed that the filtration of the alkali metal catalyst from the polymer required a filter aid to be successful. The filter aid is required for pre-coating the filter press cloth support media and further provided as a continuous feed to be mixed with the PTMEG suspension containing the variety of inorganic salts. It is widely known to use diatomaceous earth (DE) based filter aids to aid in the filtration process. However, the inventors of the present application have found that that the use of DE, which contains transition metal oxides, as a filter aid, has resulted in the leaching of transition metals catalyst species capable of possibly promoting transester formation and subsequent quality problems for downstream users of the PTMEG.

Therefore, there is a need for a filter aid that can be used in the filtration process to remove an alkali metal catalyst from a transesterification process to form a polyether polyol that does not result in transition metals catalyst species being leached in the polyol product.

SUMMARY OF THE INVENTION

Disclosed are a filter aid and a filtration process to remove an alkali metal catalyst from a transesterification process for producing a polyether polyol. The process reduces leaching of the transition metal species into the polyol product.

In a particular embodiment, the filter aid to be used a Rice Hull Ash (RHA) filter aid which contains essentially no transition metal oxide content. The RHA filter aid is successful in conjunction with the filtration process in removing the alkali metal catalyst from the polyether polyol product. It has also been found that the resultant, purified polyether polyol product contains essentially no harmful, transition metal content. An embodiment of the process comprises the steps of:

(a) providing an aqueous solution of a polyether polyol containing an alkali metal catalyst residual formed from a transesterification process utilizing an alkali metal catalyst;

(b) contacting the aqueous solution of step (a) with a stoichiometric excess of magnesium sulfate, magnesium sulfite or a combination thereof to form a second aqueous solution, wherein said stoichiometric excess is based on the amount of said alkali metal catalyst residual;

(c) removing water from said second aqueous solution of step (b) at a temperature above the melt temperature of said polyether polyol to produce a dehydrated slurry containing a molten polyether polyol phase essentially free of residual alkali metal and a precipitated solid phase comprising sulfate and/or sulfite salts of the alkali metal catalyst, magnesium hydroxide, and excess magnesium sulfate and/or sulfide;

(d) passing the dehydrated slurry of step (c) through a filtration system comprising a filter press to separate the molten polyether polyol phase from the precipitated solid phase, wherein the filtration press is treated with a filter aid with a transition metal oxide content of less than 50 ppb;

(e) separating the molten polyether polyol phase essentially free of water, residual alkali metal catalyst and transition metal contaminants from the precipitated solid phase; and (f) recovering a polyether polyol from the separated polyether polyol phase, wherein the polyether polyol has a transition metal oxide content of less than 50 ppb.

In one embodiment, the filtration press is treated with a filter aid with a transition metal oxide content of less than 10 ppb.

In another embodiment, the polyether polyol recovered in step (f) has a transition metal content of less than 10 ppb.

In another embodiment, the polyether polyol is poly(tetramethylene ether) glycol or a copolymer thereof.

In another embodiment, the alkali metal catalyst is selected from the group consisting of alkali metal hydroxide, alkali metal alkoxide, alkaline earth metal hydroxide, alkaline earth metal alkoxide, and combinations thereof, and said precipitated solid phase comprises magnesium hydroxide, sulfate salts of said alkali metal catalyst, and excess magnesium sulfate, magnesium sulfite or combinations thereof.

In another embodiment, the alkali metal catalyst is sodium methylate and said precipitated solid phase comprises magnesium sulfate, magnesium hydroxide and sodium sulfate.

In another embodiment, the filter aid is selected from a group consisting of rice hull ash (RHA), acid washed diatomaceous earth (DE) and mixtures thereof.

In another embodiment, the filter aid is rice hull ash (RHA) with a carbon content of about 5% to about 8% by weight.

In another embodiment, the rice hull ash (RHA) has a transition metal oxide content of less than 10 ppb.

BRIEF DESCRIPTION OF THE DRAWINGS

The FIGURE is a simplified schematic process diagram for an embodiment of the present invention.

DETAILED DESCRIPTION OF THE INVENTION

Disclosed is a filter aid and a filtration process to remove an alkali metal catalyst from a transesterification process for producing a polyether polyol. The process reduces leaching of transition metals into the polyol product.

All patents, patent applications, test procedures, priority documents, articles, publications, manuals, and other documents cited herein are fully incorporated by reference to the extent such disclosure is not inconsistent with this invention and for all jurisdictions in which such incorporation is permitted.

The term "polymerization", as used herein, unless otherwise indicated, includes the term "copolymerization" within its meaning.

The term "PTMEG", as used herein, unless otherwise indicated, means poly(tetramethylene ether glycol). PTMEG is also known as polyoxybutylene glycol.

The term "THF", as used herein, unless otherwise indicated, means tetrahydrofuran and includes within its meaning alkyl substituted tetrahydrofuran capable of copolymerizing with THF, for example 2-methyltetrahydrofuran, 3-methyltetrahydrofuran, and 3-ethyltetrahydrofuran.

The embodiments herein relate to an improved method for recovering purified polytetramethylene ether glycol (PTMEG) or similar polyether polyols from an aqueous polymer solution containing an alkaline metal catalyst residue. More generally, the FIGURE depicts a process diagram for an embodiment of the present invention that includes the steps of contacting an aqueous polymer solution (120) containing an alkali metal catalyst residual formed from a transesterification process utilizing an alkali metal catalyst with a stoichiometric excess of magnesium sulfate, magnesium sulfite or a combination thereof (160) and water (140) in a mixer (100) to form a second aqueous solution (180). This is followed by dehydrating (200, 300) the second aqueous solution (180) through the effective evaporation of water (240, 320) to form a dehydrated slurry (220,340) containing a molten polyether polyol phase substantially free of residual alkali metal and a precipitated solid phase comprising sulfate and/or sulfite salts of the alkali metal catalyst, magnesium hydroxide, and excess magnesium sulfate and/or sulfide. The FIGURE depicts a 2-stage dryer system (200,300). Other embodiments of the present invention may include a single dryer or multiple drying stages to effectively remove water from the second aqueous solution (180). Drying can be performed at reduced pressure and typically 140 degree C. Drying and crystallization take place ahead of filtration of the inorganic solids from PTMEG, which is carried out in a continuous filter press (500) in the manner herein described.

The dehydrated slurry (340) is passed through a filtration system comprising a filter press (500) to separate the molten polyether polyol phase from the precipitated solid phase, wherein the filter press is treated with a filter aid (360) that is essentially free of transition metal content. The filter aid may contain a transition metal oxide content of less than 50 ppb, and more preferably less than 10 ppb. This press contains a main frame and several recessed chamber plates which are clothed in filter fabric prior to the commencement of the filtration process. Prior to filtration, a slurry of clean PTMEG (520) and filter aid (360) is processed through these plates to deposit a layer of filter aid precoat to arrest fine particulate matter and thus avoid blinding the filter cloth when the primary solids are deposited.

In this embodiment of the present invention, the use of rice hull ash (RHA) as a filter aid (360) promotes essentially complete removal of basic trans-esterification catalysts (540) present with only minor significant loss of the polyether polyol product. At the end of the precoat operation, signaled by clear PTMEG at the operation exit (520), the PTMEG slurry is continuously mixed with RHA and fed to the press. The press filtration separates the PTMEG from the inorganic impurities. Filtration rate is enhanced by pressure and higher temperatures (i.e. 110 to 120 degrees C.) to maintain a free flowing polymer. The polymer stream leaving the filter press (520) is clear as determined by an on-line turbidity meter and sampling with alkalinity analysis to ensure that the inorganic impurities have been filtered out. As the solids accumulate in the recessed chamber, the pressure drop increases gradually. A life-time of the filter press is determined when the pressure drop reaches a value dictated by the limitations of the unit operation, as one skilled in the art would understand. The PTMEG product (520), which is substantially free of transition metal contaminants, can be employed in critical end-use applications for making polyurethanes and polyester elastomers.

The applicants have found RHA to be effective in separating the inorganic impurities from PTMEG. As a result, the use of rice hull ash is preferred over diatomaceous earth and other similar silicaceous mineral based filter aids to eliminate PTMEG quality problems. Such problems have been long associated with transition metal contaminants leaching from other types of filter aids and causing discoloration or accelerating undesired side reactions. In the practice of the process embodiment herein disclosed, transition metal contaminants were reduced to levels less than 10 parts per billion (ppb).

Consequently, it was discovered that rice hull ash (RHA) could be employed as a viable filter aid application for PTMEG process to remove alkaline solids at low cost without the transition metal contamination issue. Whereas a diatomaceous earth (DE) based filter aid seemed to be the root cause of PTMEG quality problems owing to trace amounts of transition metals. This contamination was found to result from the use of DE. The color problems and reactivity we observed at levels of transition metal species in the range of about 50 to about 100 parts per billion (ppb) in the filtrate glycol. In other embodiments of the present invention, an acid washing of the DE filter aid was also found to resolve the transition metal contamination in the PTMEG. The acid washed DE filter aid represents a higher costing and less practical option than the use of RHA as a filter aid. The RHA used in a preferred embodiment of the current invention contains less than 50 ppb of transition metal oxide content, and more preferably less than 10 ppb.

Rice hull ash (RHA) filter aid is produced by burning rice hulls to produce an ash with the silica content between 92% and 95%, the balance primarily carbon black. The inventors have found significant advantages when utilizing RHA with carbon content in the range of from about 5% to about 8%. Inadequate burning, which results in a carbon content greater than 8%, leaves excess carbon on the RHA. As a result, the filter cake formed is more compressible and leads to rapid increase in pressure drop, which is undesirable. Furthermore, over burning of the RHA, which results in a carbon content less than 5%, leads to fusion of the residual mineral content in the RHA, loss of micro-porosity, and less effective function as a filter aid. In addition, it has been found that yet another benefit of burning the RHA to a carbon content of between 5 to 8 wt % is that there is a reduced risk of dust cloud explosions. RHA also contains traces of potassium salts but not transition metal oxides. The ground RHA is then classified to remove oversized particles and the black solids collected. The fines in the filter aid are also removed to reduce the personnel exposure to dust during handling.

Table 1 below illustrates suitable values for certain process operating values.

TABLE 1

| | | Units | Narrower range Min | Narrower range Max | Broader range Min | Broader range Max |
|---|---|---|---|---|---|---|
| 1 | Transition metal oxides | Ppb[1] | 0 | 10 | 0 | 25 |
| 2 | Filter Press Pressure | Psi | 10 | 120 | 10 | 150 |
| | Filter Press temperature | °C. | 100 | 120 | 100 | 140 |
| 3 | Filter aid addition | Wt % | 0.14 | 0.20 | 0.14 | 0.25 |
| 4 | Filter aid particle size | $d_{90}^2$ | 450μ | 510μ | 450μ | 560μ |
| | | $d_{10}^3$ | 65μ | 75μ | 65μ | 85μ |
| | | $d_2^4$ | 8μ | 10μ | 8μ | 12μ |
| | | Mean | 190 | 210 | 190 | 230 |
| 5 | Stoichiometric excess | % excess[5] | 100 | 200 | 100 | 300 |

EXAMPLES

The following Examples demonstrate the present invention and its capability for use. The invention is capable of other and different embodiments, and its several details are capable of modifications in various apparent respects, without departing from the scope and spirit of the present invention. Accordingly, the Examples are to be regarded as illustrative in nature and non-limiting.

Example 1

An online turbidity meter, as known to one skilled in the art, is adequate to test the success of the filter operation by ensuring that no solids bypass the filter. The filtered product is analyzed to ensure all the inorganic impurities are removed by measuring the alkalinity number of the product as a primary verification of quality. Rice hull ash is used in a pressure filter to remove alkaline earth and alkali metal salts to below the max 1.0 alkalinity number. The pressure in the filter press is typically increased to 100 to 110 psi to maintain flux through the filter cake over the lifetime of the filter. The polymer product exits the filter below maximum allowed 1.0 alkalinity number.

Table 2 shows that the transition metal contamination is significantly lowered with the use of RHA as a filter aid, while maintaining an allowed alkalinity number. The filter material used in this example is 1000-2000 grade Terathane® PTMEG Dryer Feed from INVISTA's LaPorte facility. The filter press was maintained at temperature from 110° C. to 120° C. The precoat application of filter aid applied to the filter press was 0.1 lb/ft² and the body feed was a 2% filter aid slurry.

TABLE 2

| Filter Aid Used | Filter Aid Transition Metal Oxide Content (ppm) | Transition Metal Oxide Content in PTMEG (ppb) | Filtrate Alk. No. |
|---|---|---|---|
| diatomaceous earth (DE) | 250 | 261 | +0.02 |
| SSC (H₂O Wash) | 170 | 32 | +0.10 |
| Rice Hull Ash (carbon content of about 5% to about 8% by weight) | 5 | 6 | +0.06 |

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also the individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±8%, or ±10%, of the numerical value(s) being modified. In addition, the phrase "about 'x' to 'y'" includes "about 'x' to about 'y'".

While the illustrative embodiments of the invention have been described with particularity, it will be understood that the invention is capable of other and different embodiments and that various other modifications will be apparent to and may be readily made by those skilled in the art without departing from the spirit and scope of the invention. Accordingly, it is not intended that the scope of the claims hereof be limited to the examples and descriptions set forth herein but rather that the claims be construed as encompassing all the features of patentable novelty which reside in the present disclosure, including all features which would be treated as equivalents thereof by those skilled in the art to which the invention pertains.

What is claimed is:

1. A method for recovering a purified polyether polyol comprising the steps of:
   (a) providing an aqueous solution of a polyether polyol containing an alkali metal catalyst residual formed from a transesterification process utilizing an alkali metal catalyst;
   (b) contacting the aqueous solution of step (a) with a stoichiometric excess of magnesium sulfate, magnesium sulfite or a combination thereof to form a second aqueous solution, wherein said stoichiometric excess is based on the amount of said alkali metal catalyst residual;
   (c) removing water from said second aqueous solution of step (b) at a temperature above the melt temperature of said polyether polyol to produce a dehydrated slurry containing a molten polyether polyol phase essentially free of residual alkali metal and a precipitated solid phase comprising sulfate and/or sulfite salts of the alkali metal catalyst, magnesium hydroxide, and excess magnesium sulfate and/or sulfide;

(d) passing the dehydrated slurry of step (c) through a filtration system comprising a filter press to separate the molten polyether polyol phase from the precipitated solid phase, wherein the filtration press is treated with a filter aid with a transition metal oxide content of less than 50 ppb;

(e) separating the molten polyether polyol phase essentially free of water, residual alkali metal catalyst and transition metal contaminants from the precipitated solid phase; and (f) recovering a polyether polyol from the separated polyether polyol phase, wherein the polyether polyol has a transition metal oxide content of less than 50 ppb;

wherein said filter aid is selected from a group consisting of rice hull ash (RHA), acid washed diatomaceous earth (DE) and mixtures thereof.

2. The method of claim 1 wherein the filtration press is treated with a filter aid with a transition metal oxide content of less than 10 ppb.

3. The method of claim 1 or claim 2 wherein the polyether polyol recovered in step (f) has a transition metal content of less than 10 ppb.

4. The method of claim 1 wherein said filter aid is rice hull ash (RHA) with a carbon content of about 5% to about 8% by weight.

5. The method of claim 1 wherein said polyether polyol is poly(tetramethylene ether) glycol or a copolymer thereof.

6. The method of claim 1 wherein said alkali metal catalyst is selected from the group consisting of alkali metal hydroxide, alkali metal alkoxide, alkaline earth metal hydroxide, alkaline earth metal alkoxide, and combinations thereof, and said precipitated solid phase comprises magnesium hydroxide, sulfate salts of said alkali metal catalyst, and excess magnesium sulfate, magnesium sulfite or combinations thereof.

7. The method of claim 1 wherein said alkali metal catalyst is sodium methylate and said precipitated solid phase comprises magnesium sulfate, magnesium hydroxide and sodium sulfate.

* * * * *